United States Patent
Kuhnke (12)

(10) Patent No.: US 6,295,127 B1
(45) Date of Patent: Sep. 25, 2001

(54) APPARATUS FOR MEASURING CAN SEAMS

(76) Inventor: Manfred Kuhnke, Sperberfeld 29, 14532 Kleinmachnow (DE)

( * ) Notice: Subject to any disclaimer, the term of this patent is extended or adjusted under 35 U.S.C. 154(b) by 0 days.

(21) Appl. No.: 09/598,116

(22) Filed: Jun. 21, 2000

(30) Foreign Application Priority Data

Jun. 28, 1999 (DE) .............................................. 199 30 536

(51) Int. Cl.$^7$ .................................................. G01N 21/00
(52) U.S. Cl. ...................................... 356/240.1; 348/127
(58) Field of Search ............................. 356/240.1, 239.4, 356/397, 394, 634–636; 250/223 R, 223 B; 348/125, 127; 33/522; 209/580, 587, 597

(56) References Cited

U.S. PATENT DOCUMENTS

| | | | | |
|---|---|---|---|---|
| 5,017,795 | * | 5/1991 | Dower et al. ......................... | 356/385 |
| 5,104,226 | * | 4/1992 | Eble et al. ......................... | 356/240.1 |
| 5,200,801 | * | 4/1993 | Juvinall et al. .................... | 356/240.1 |
| 5,220,400 | * | 6/1993 | Anderson et al. .................... | 250/572 |
| 5,249,034 | * | 9/1993 | Minato ................................ | 356/375 |
| 5,386,293 | * | 1/1995 | Barnard et al. ...................... | 356/397 |
| 6,133,999 | * | 10/2000 | Myers et al. ....................... | 356/239.4 |

FOREIGN PATENT DOCUMENTS 09-21762 * 1/1997 (JP).
09-33238 * 2/1997 (JP).

OTHER PUBLICATIONS

Article entitled "Video Seam Monitor VSM III" published by Kuhnke Can & End Testing Equipment, 4 pp.

* cited by examiner

*Primary Examiner*—Hoa Q. Pham
(74) *Attorney, Agent, or Firm*—Cohen, Pontani, Lieberman & Pavane

(57) ABSTRACT

Disclosed is an apparatus for measuring a can seam, wherein the seam of a can positioned on a measuring table by way of the seam, sawn open radially in a segment-like manner at least two to three times on the circumference, is monitored and measured by means of a video camera and a lighting device. With the avoidance of a deflecting element in the optical beam path within the can, the camera lens and the lighting unit are aligned with the can seam, which is inserted into a depression of the measuring table, the depression corresponding to the can diameter, such that the free view of the camera falls, in the tangential direction to the seam circumference, directly on the saw-cut surface of the seam. A stop pin alongside the saw-cut surface fixes the focusing point of the camera lens on the cut surface.

7 Claims, 1 Drawing Sheet

APPARATUS FOR MEASURING CAN SEAMS

BACKGROUND OF THE INVENTION

The invention relates to an apparatus for measuring can seams, by means of which the seam of a can positioned on a measuring table by way of the seam, the latter being sawn open radially in a segment-like manner at least two to three times on the circumference, can be monitored and measured by means of a video camera and a lighting device.

The sealing of cans is ensured by correct sealing of the seam by connecting the top to the body of the can. It is thus necessary to randomly sample filled cans from an ongoing production as random samples, and saw open the seam in a segment-like manner two to three times on the circumference and to monitor the interior dimensions of the seam.

In the filling of drinks into cans using high-performance can-filling equipment with, for example, from 22 to 28 filling stations, it is necessary for at least one can per station and shift to be randomly sampled for a seam recheck. In each case seven features are measured on the can seam, which is sawn open three times on the circumference, i.e., with 22 stations and three shifts and 7 features, 462 measurements are determined per shift. Automation of this monitoring operation would thus save a substantial amount of time and improve the economics.

Previously, with the aid of a prism or deflecting mirror projecting into the free, sawn-open segment of the can, it has been practice to align perpendicularly the optical path of the viewing lens with the seam surface of the can, moved manually into the respective measuring position, and for the seam cross section either to be projected purely optically onto a viewing screen, and measured directly there, or to be transmitted from a video camera to a monitor and measured by mouse control using a suitable computer program (SEAM PROJECTOR DP1 brochure from Manfred Kuhnke Optische Meβ-und Kontrollapparate, Berlin and VIDEO SEAM MONITOR VSM III brochure from KUHNKE Can & End Testing Equipment, Berlin).

The liquid contents of drink cans must be emptied before the cans can be sawn open. It is not possible to prevent any remaining liquid contents from running out from the saw cut during measurement and soiling the deflecting mirror or the prism and thus adversely influencing the measurement result.

The measurement results may be further adversely affected by extraneous light.

These two mentioned adverse effects present an obstacle to automation of the measuring operation.

SUMMARY OF THE INVENTION

An object of the invention is to provide an apparatus for the optical measurement of can seams such that the measurement result is not adversely affected either by residual liquid running out of the can or by extraneous light, and thus to allow the measuring operation to be largely automated.

This object is achieved according to the invention in that, with the avoidance of a deflecting element in the optical beam path within the can, the camera lens and the lighting unit are aligned with the can seam, which is inserted into a depression of the measuring table, the depression corresponding to the can diameter, such that the free view of the camera falls, in the tangential direction to the seam circumference, directly on the saw-cut surface of the seam. A retractable stop pin alongside the saw-cut surface fixes the focusing point of the camera lens on the cut surface.

In another embodiment of the invention, the system includes a positioning drive which interacts with the retractable stop pin for the saw-cut surface to rotate the can from one saw-cut surface to the next and the stop pin can be retracted electromagnetically counter to a spring force.

In another embodiment of the invention, the video camera digitally transmits the image taken of the seam to a monitor, and the image is measured with the aid of a specific computer program, each measuring operation starting as soon as the respective saw-cut surface of the seam is located in the focusing region of the lens or of the camera.

An advantage of the invention is that a semiautomatic seam measurement is obtained with a relatively low outlay in technical and material terms.

The various features of novelty which characterize the invention are pointed out with particularity in the claims appended to and forming a part of this specification. For a better understanding of the invention, its operating advantages and specific objects obtained by its use, reference should be had to the accompanying drawings and descriptive matter in which there is illustrated and described a preferred embodiment of the invention.

DETAILED DESCRIPTION OF THE PRESENTLY PREFERRED EMBODIMENTS

Figure 2:
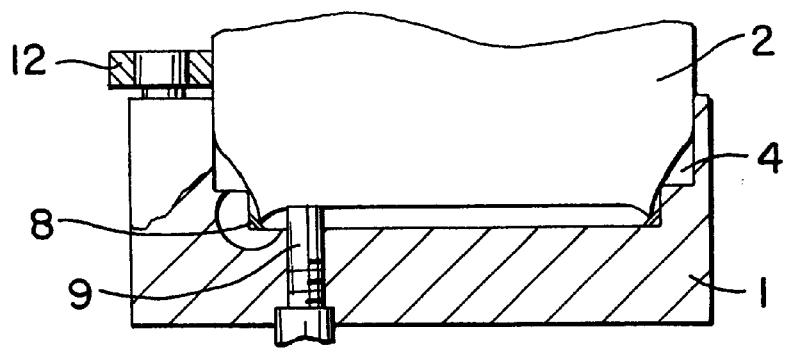
FIG. 2 shows a section of the apparatus along view line A–B of FIG. 1.
Figure 1:
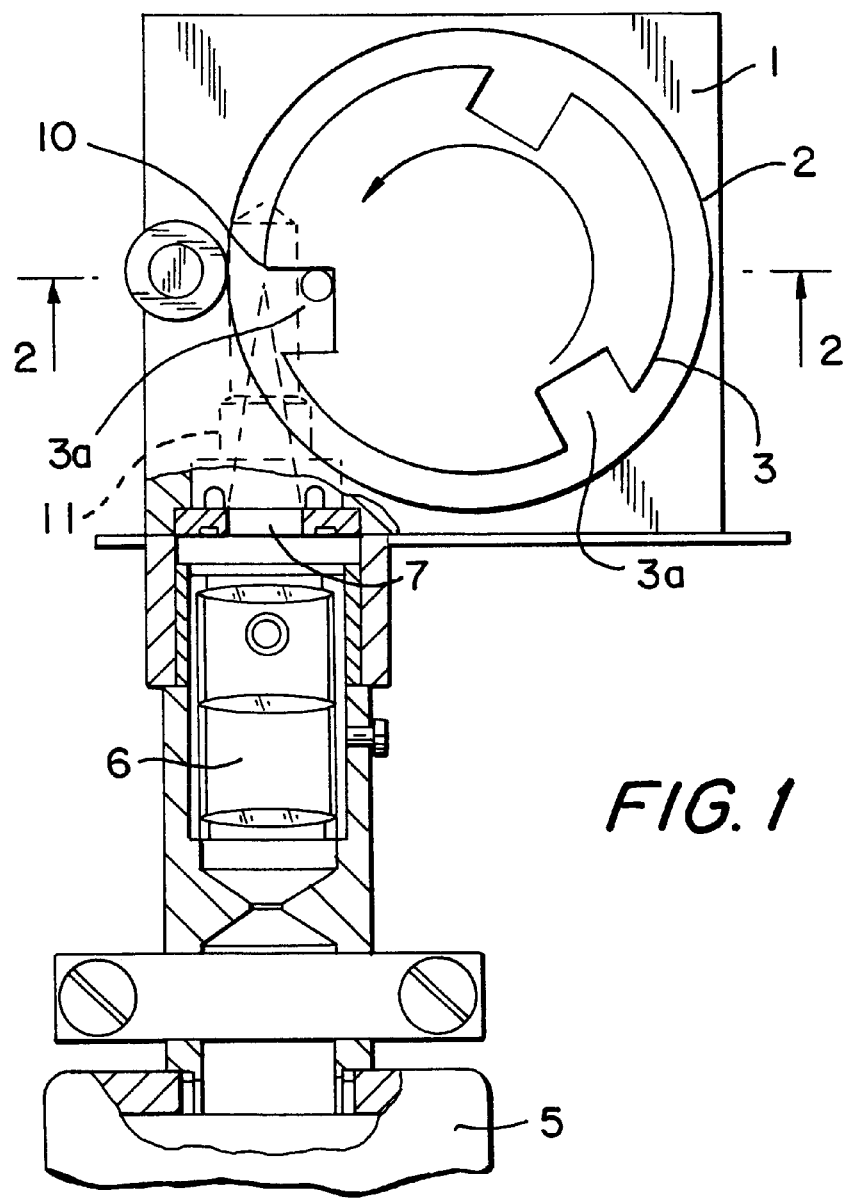
FIG. 1 shows a partially sectional partial plan view of an apparatus of the invention for measuring can seams.

FIG. 1 illustrates only those mechanical and optical parts of the measuring apparatus which are essential for the purpose of explaining the invention.

FIG. 1 shows a measuring table 1 with a can 2 which is positioned thereon and of which the seam 3 is inserted into a depression 4 of the measuring table 1. The depression 4 is dimensioned to correspond to the can diameter. The seam 3 is sawn open radially in a segment-like manner three times on the circumference by means of a saw (not shown).

A video camera 5 with lens 6 and a lighting unit 7, in this case an LED ring, are arranged laterally on the measuring table 1 and are aligned with the can seam 3 such that, by way of a stepped bore 11, the free view of the camera 5 falls, in the tangential direction to the seam circumference, directly on the saw-cut surface 8 of the seam 3. A stop pin 9 alongside the saw-cut surface 8 fixes the focusing point 10 of the camera lens 6 on the cut surface 8.

The stop pin 9 can be retracted electromagnetically counter to a spring force (not shown) and interacts with a positioning drive 12 which is provided for the purpose of rotating the can 2, which is inserted into the depression 4 of the measuring table 1, from one saw-cut surface 8 to the next.

The video camera 5 digitally transmits the image of the seam to a monitor, and the measuring of the image is performed with the aid of a specific computer program, each measuring operation starting as soon as the respective saw-cut surface 8 of the seam 3 is located in the focusing region of the lens 6 or of the camera 5.

The terms and expressions which have been employed are used as terms of description and not of limitation, and there is no intention in the use of such terms and expressions of excluding any equivalent of the features shown and described or portions thereof, it being recognized that various modifications are possible within the scope of the invention.

I claim:

1. An apparatus for measuring a can seam comprising:

a measuring table having a depression therein, said depression having a dimension corresponding to a can diameter to receive said can;

a lighting unit;

a video camera having a lens, wherein, with the avoidance of a deflecting element in an optical beam path within the can, the camera lens and the lighting unit are aligned with the can seam, such that the free view of the camera falls, in the tangential direction to the seam circumference, directly on a saw-cut surface of the seam; and a stop pin alongside the saw-cut surface fixing the focusing point of the camera lens on the cut surface.

2. The apparatus of claim 1, wherein the stop pin is retractable.

3. The apparatus of claim 2, further comprising a positioning drive which interacts with the retractable stop pin for the saw-cut surface to move the can from one saw-cut surface to the next.

4. The apparatus of claim 2, wherein the stop pin is retractable electromagnetically counter to a spring force.

5. The apparatus of claim 1, wherein the video camera digitally transmits the image of the seam to a monitor.

6. The apparatus of claim 5, wherein the measuring of the image is performed with the aid of a specific computer program.

7. The apparatus of claim 6, wherein each measuring operation commences when the respective saw-cut surface of the seam is located in the focusing region of the lens or of the camera.

* * * * *